(12) United States Patent
Duray et al.

(10) Patent No.: US 11,471,687 B2
(45) Date of Patent: Oct. 18, 2022

(54) METHOD AND APPARATUS FOR RECOVERING AND STABILIZING NORMAL HEART RATE OF PATIENTS SUFFERING IN OR BEING INCLINED TO HAVING ATRIAL FIBRILLATION

(71) Applicants: Gábor Duray, Budapest (HU); Lajos Mancsiczky, Debrecen (HU); László Major, Gyál (HU)

(72) Inventors: Gábor Duray, Budapest (HU); Lajos Mancsiczky, Debrecen (HU); László Major, Gyál (HU)

( * ) Notice: Subject to any disclaimer, the term of this patent is extended or adjusted under 35 U.S.C. 154(b) by 0 days.

(21) Appl. No.: 16/093,109

(22) PCT Filed: Dec. 4, 2017

(86) PCT No.: PCT/HU2017/050011
§ 371 (c)(1),
(2) Date: Oct. 11, 2018

(87) PCT Pub. No.: WO2017/178851
PCT Pub. Date: Oct. 19, 2017

(65) Prior Publication Data
US 2020/0330770 A1    Oct. 22, 2020

(51) Int. Cl.
| | | |
|---|---|---|
| *A61N 1/36* | (2006.01) |
| *A61N 1/368* | (2006.01) |
| *A61N 1/39* | (2006.01) |
| *A61N 1/05* | (2006.01) |
| *A61N 1/362* | (2006.01) |
| *A61N 1/375* | (2006.01) |

(52) U.S. Cl.
CPC .......... *A61N 1/36843* (2017.08); *A61N 1/059* (2013.01); *A61N 1/3624* (2013.01); *A61N 1/3756* (2013.01); *A61N 1/395* (2013.01); *A61N 1/39622* (2017.08)

(58) Field of Classification Search
CPC ............ A61N 1/36843; A61N 1/39622; A61N 1/059; A61N 1/3624; A61N 1/3756; A61N 1/395; A61N 1/3684; A61N 1/3622; A61N 1/365; A61N 1/3962; A61N 1/0587; A61N 1/368; A61N 1/372; A61N 1/375
See application file for complete search history.

(56) References Cited

U.S. PATENT DOCUMENTS

| | | | | |
|---|---|---|---|---|
| 5,800,465 A | * | 9/1998 | Thompson | A61N 1/368 607/9 |
| 6,937,895 B1 | * | 8/2005 | Lu | A61N 1/3684 607/9 |
| 7,647,108 B2 | * | 1/2010 | Freeberg | A61N 1/3712 607/28 |

(Continued)

*Primary Examiner* — Rex R Holmes
(74) *Attorney, Agent, or Firm* — Handal & Morofsky, LLC; Anthony H. Handal

(57) ABSTRACT

Method for recovering and stabilizing normal heart rate of patients suffering in or being inclined to having atrial fibrillation, comprising the step of sensing primary electrical pulses generated in the right atrium (1), of generating artificial electrical stimulation pulses coordinated with the sensed pulses and stimulating therewith the portion of the left atrium (9) which is remote from the right atrium (1), whereby increasing the areas of the heart muscles that can be reached during a simulation pulse within a predetermined period of time.

14 Claims, 10 Drawing Sheets

(56) References Cited

U.S. PATENT DOCUMENTS

| | | | | |
|---|---|---|---|---|
| 7,941,217 B1* | 5/2011 | Pei | ............... | A61N 1/365 |
| | | | | 607/9 |
| 8,634,919 B1* | 1/2014 | Hou | ............... | A61N 1/368 |
| | | | | 607/36 |
| 2003/0069609 A1* | 4/2003 | Thompson | ......... | A61N 1/39622 |
| | | | | 607/14 |
| 2013/0123872 A1* | 5/2013 | Bornzin | ............ | A61N 1/37205 |
| | | | | 607/17 |
| 2017/0106191 A1* | 4/2017 | Pei | ............... | A61N 1/3622 |

* cited by examiner

METHOD AND APPARATUS FOR RECOVERING AND STABILIZING NORMAL HEART RATE OF PATIENTS SUFFERING IN OR BEING INCLINED TO HAVING ATRIAL FIBRILLATION

A method and apparatus for recovering and stabilizing normal heart rate of patients suffering in or being inclined to having atrial fibrillation The invention relates to a method and apparatus for recovering and stabilizing normal heart rate of patients suffering in or being inclined to having atrial fibrillation.

There are several known published methods for the treatment of atrial fibrillation. One of the recognized procedures for the reduction of occurrence of atrial fibrillation is the atrial pacing by means of dual chamber pacemaker on patients who require pacemaker implantation (New approaches to atrial fibrillation management: A critical review of a rapidly evolving field. Nattel S1, Khairy P, Roy D, Thibault B, Guerra P, Talajic M, Dubuc M. PubMed).

Further known methods include catheter ablation treatment of atrial fibrillation as disclosed in US 20083064477 A1 and US 2005228468 A1 that use the destruction of the tissues triggering the abnormal heart rhythm at the site of induction and on the electric pathway of abnormal pacing stimuli in the left atrium. The efficiency is around 70%.

Animal experiments on dogs have confirmed that multi-site left atrial pacing reduced the risk of onset of atrial fibrillation (High-density biatrial pacing protects against atrial fibrillation by synchronizing left atrial tissue. Hansen J C1, Latchamsetty R, Lavi N, Uppuluri S, Lafontaine D, Hastings R, Avitall B. J Intery Card Electrophysiol. 2010 March; 27(2):81-7. doi: 10.1007/s10840-009-9453-0. Epub 2009 Dec. 9.). In these dog experiments they did not stimulate the left appendage at the farthest site of left atrium. Otherwise, it is stated in this publication, that the initial foci of the atrial fibrillation are located in the substrate at pulmonary veins and in the left atrium. Essentially they prepared the ground for the method of ablation of pulmonary veins; however, they did not recognize the problem of ablation method, namely the inevitably accompanying recurrence.

The basic principle of the procedures used up the present was the assumption that atrial fibrillation is initiated by autonomic ectopic pacemaker foci that should be destroyed and isolated as an appropriate therapy. Later it turned out that new foci can frequently wake up activating an arrhythmia again.

The currently available heart rate control devices (pacemakers) offer intervention at minimum one locus of stimulation, which is applied generally in the right ventricle, and most frequently in the right atrium and in the right ventricle, and in given cases also in the left ventricle. In the currently used pacemakers there are a few ways how the electrode leads can be fixed in the different heart cavities, and these include active means (typically screws and tined or hooked tip) and passive ones (typically electrically passive plastic and/or silicone tined tip).

Traditional cardiac surgical methods are used for the fixation of leads on the external surface of the atrium with mini-thoracotomy or with any other minimal invasive technique.

There are also known leadless heart rate control devices which are fully implanted in the heart and which operate in a self standing way, they detect and sense the ECG in the associated heart cavity and based thereon they deliver controlled pulses (Reynolds D, Duray G Z, Omar R, Soejima K, Neuzil P, Zhang S, Narasimhan C, Steinwender C, Brugada J, Lloyd M, Roberts P R, Sagi V, Hummel J, Bongiorni M G, Knops RE, Ellis C R, Gornick C C, Bernabei M A, Laager V, Stromberg K, Williams E R, Hudnall J H, Ritter P; Micra Transcatheter Pacing Study Group. A Leadless Intracardiac Transcatheter Pacing System, N Engl J Med. 2016 Feb. 11; 374 (6): 533-41. doi: 10.1056/NEJMoa1511643. Epub 2015 Nov. 9.).

The primary object of the present invention is to provide a minimum invasive method and apparatus which restores or stabilizes the normal heart rate if patients suffering in or inclined to having atrial fibrillation by the generation of electrical stimuli applied in appropriate moments and in appropriate loci.

In the basic case this can be realized by the coordinated artificial stimulation in the appropriate moments of the farthest point of the left atrium, of the left appendage and in case of need other points of the left atrium.

It has been recognized that in case of atrial fibrillation the balance gets upset between the conductance of the stimulation, the subsequent refractory period (when the stimulation has no effect) and the atrial size (i.e. the muscular area that can be safely stimulated by a single stimulation). The collapse of such a balance will automatically open a way to the effects of spontaneous stimulating foci. Consequently after an ablation new (previously suppressed or over controlled) centres can get activated and the arrhythmia can start again, since heart muscle cells have congenital tendency to be able to generate spontaneous stimuli with different rate.

It has been recognized that in case of atrial fibrillation in the heart there is certain proportionality between the conductance of the stimulation, the refractory period and the size of the atria and on the required number of stimulating electrodes.

It has also been recognized that the actual effect of the ablation/isolation of the pulmonary veins lies in decreasing the portion of the electrically active muscle area primarily that extends over the left atrium, whereby it can restore the proportion between the atrial sizes, the conductance of the stimulation and the refractory period. The direction of the invasive treatment of atrial fibrillation should not be the ablation and pulmonary isolation but the restoration of the synchronous operation of the atrial muscles, i.e. the atrial resynchronization primarily by the stimulation of the appendage of the left atrium and in case of need of its other area portions.

It has also been recognized that the simultaneous (synchronic) stimulation of the left and right atria is not sufficiently efficient for eliminating the fibrillation, and in part of the cases a different timing of the stimulation of the two atria is required so that the stimulation can be set according to the delay of signal passage through the tissues.

It has also been recognized that in case of atrial fibrillation or other atrial arrhythmias there is a need of overdrive stimulation at the atrial stimulation sites for the termination of the arrhythmia. The resynchronizing treatment takes place directly for the prevention or treatment of atrial fibrillation and for the correction of the established diseased anatomy and atrial function, which can be realized by the direct and permanent stimulation of the remote parts of the left atrium (preferably of the left appendage) and other discrete sites.

Based on the aforementioned recognitions the object of the invention has been attained by providing a method for recovering and stabilizing normal heart rate of patients suffering in or being inclined to having atrial fibrillation, which comprises the step of sensing primary electrical pulses generated in the right atrium, and according to the invention also comprising the steps of generating artificial electrical stimulation pulses coordinated with the sensed pulses and stimulating therewith the portion of the left atrium which is remote from the right atrium, whereby increasing the areas of the heart muscles that can be reached during a simulation pulse within a predetermined period of time.

During the aforementioned coordination the artificial stimulation pulses are delayed by a predetermined period with respect to the sensed primary pulses in most of the cases.

It is preferred if the left appendage or an adjacent heart muscle areas are stimulated with the artificial pulses In case of certain anatomic situations the artificial electrical stimulating pulses are lead to a plurality of distinct portions of the left atrium, in which the number of said portions is chosen based on the ratio of certain parameters of a healthy heart to the same measured parameters of the patient under treatment.

In this case the measured parameters of the treated patient include the longest conduction time between the right and left atrium, the refractory period, and the largest diameter of the atria and these measured parameters are compared to the normal values of these parameters, and the number of the stimulated portions will be the integer which is closest to the product of this ratios.

In a preferred embodiment of the method the stimulating pulses are lead to an electrode or electrodes contacting directly these portions.

In a different preferred embodiment at least one of the stimulation is carried out by a leadless stimulating device placed in the left appendage and the device has electrodes contacting the inner wall of the appendage.

In a preferred embodiment the artificial pulses are delayed by a period of at most 150 ms, and the delay is controlled on the basis of the examination of the intracardial atrial activation time and it minimum value is adjusted.

When the stimulation is carried out by a leadless device, there is no possibility for the direct measurement of the intracardial atrial activation time, therefore the possible extent of the delay is based on the measured width of the P wave of the ECG of the patient and this width is minimized.

The security is increased when no primary electrical pulse is sensed in the right atrium then these pulses are generated and in case of need the right and left ventricles are also stimulated.

According to the invention an apparatus has also been provided for recovering and stabilizing normal heart rate of patients suffering in or being inclined to having atrial fibrillation, which can be positioned in the body of the patient and comprises a lead or leadless electrode placed in the right atrium that senses the primary electrical pulses generated therein and comprises a sensing unit coupled to this electrode and also comprises a pulse generator that generates stimulating pulses in moments related to the time of occurrence of the sensed primary pulses, the pulse generator is in wired or leadless connection with a further electrode and according to the invention the pulse generator generates stimulating pulses being offset in time relative to the moments of the primary pulses, or in special situation coincide therewith, and during operation the electrode controlled by these stimulating pulses contacts a portion of the heart of the treated patient lying remotely from the right atrium.

In most of the cases the offset in time is an at most 150 ms long delay.

A preferred embodiment comprises a unit for controlling the moments of the generated pulses that senses the intracardial activation time and/or the P wave of the heart of the patient, and adjusts the timing to the minimum or close to the minimum of the activation time and/or the width of the P wave or it enables the manual adjustment of the same.

It is preferred if the pulse generator has a plurality of outputs by which different portions of the left atrium of the patient are stimulated, and respective slightly differing delay times are associated with the stimulating pulses of the respective outputs.

It is preferred if the apparatus further comprises a pacemaker unit in addition to the generation of the stimulating pulses, and the pacemaker unit has outputs connected to the electrode of the right ventricle and to the electrode of the left ventricle.

It is further preferred if the pulse generator is also equipped with providing a defibrillation function and the apparatus also includes a defibrillation electrode.

A preferred embodiment comprises a leadless stimulating device that stimulates the left atrium and the device has a sufficiently small size to be placed in the left appendage and leads stimulating pulses to the wall of the surrounding appendage upon control by the pulse generator.

In this embodiment it is preferred if the stimulating device comprises legs that stabilize, position and fix the arrangement of the device in the left appendage, and the legs are abutting the inner wall of the appendage and the legs tend to expand in a flexible way and can be squeezed by a ring.

The leadless stimulating device comprises preferably an electrode or pluralities of electrodes which are biased in a flexible way to the inner wall of the appendage and which open up or extend in a resilient way in a direction opposite to the fixing legs.

It is preferred if the opening of the appendage is closed by a closing plate and/or closing plug and/or a Watchman closing device.

It is preferred if a hook or fixing screw element or a connection filament is coupled to the rear end part of the stimulating device arranged in the appendage.

In case of wired contacts the electrode can be coupled to the exterior of the heart wall and this electrode comprises an initially rolled then opened suction disc that can be positioned to a targeted portion of the heart wall, a suction tube is coupled to the a central opening of the suction disc and a wire is lead in the interior of the suction tube, and an electrode hook is provided at the tip of the wire, and when the suction disc gets sucked, the electrode hook is pressed in the wall of the heart in a given depth where it stops and gets into electrical contact with the heart wall.

It is preferred if the suction disc comprises an elongated central opening.

In an alternative embodiment the electrode can be coupled to the exterior of the heart wall and the electrode is designed as an electrode clip fixing the position of the electrode and being biased by a spiral spring, and the electrode clip comprises a plurality of circularly arranged clench tips having forward edges bent towards the heart wall, and the clench tips tend to get flexibly expanded and they are surrounded by a ring, and the retraction of the clench tips with respect to the ring pushes the edges of the clench tips into the heart muscles and provides a durable contact therewith.

In a different embodiment the electrode can be coupled to the exterior of the heart wall, the electrode is biased by a spiral spring and comprises electrode tines or harpoons at their tips that can be pushed in forward direction to get penetrated into the heart wall and to establish a durable contact therewith.

The method according to the invention and the apparatus required to carry out the method will be described in connection with examples wherein reference will be made to the accompanying drawings. In the drawing.

Figure 4:
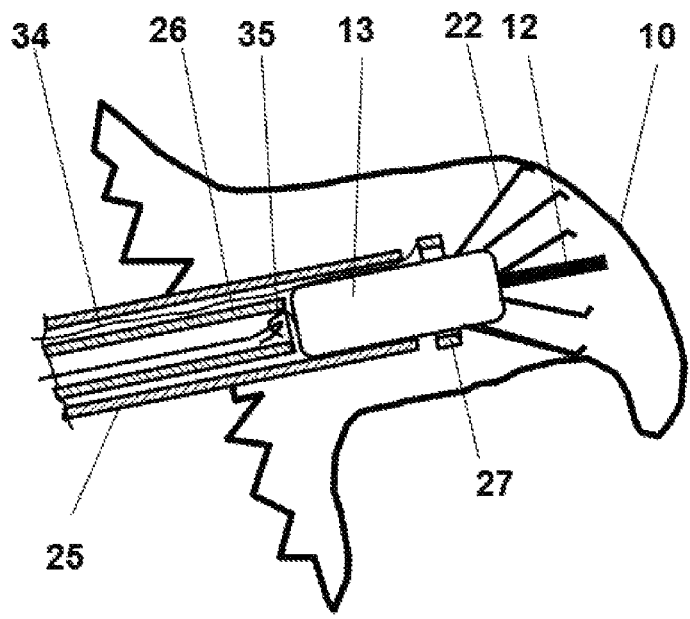
FIG. 4 shows a possible positioning and fixing of a leadless stimulating device 13 into the left atrial appendage.
Figure 5:
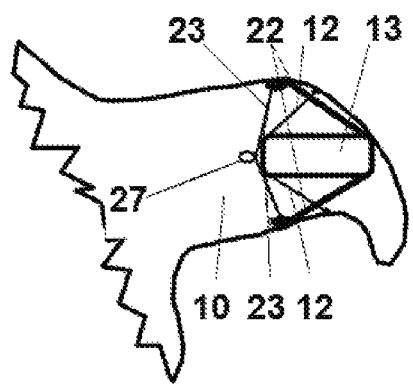
FIG. 5 shows the stimulation device 13 of FIG. 4 following the removal of the introductory means.
Figure 6:
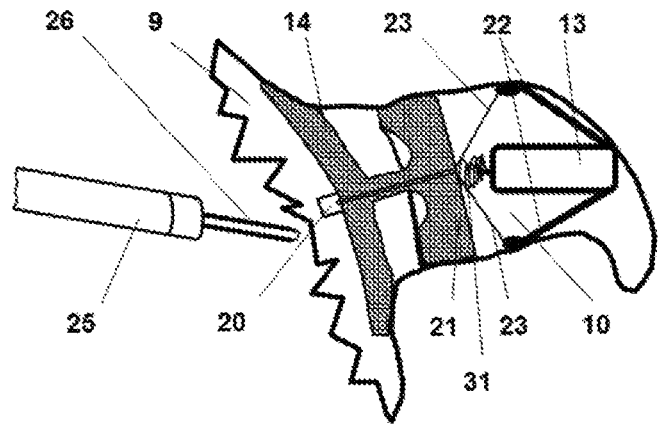
Figure 7:
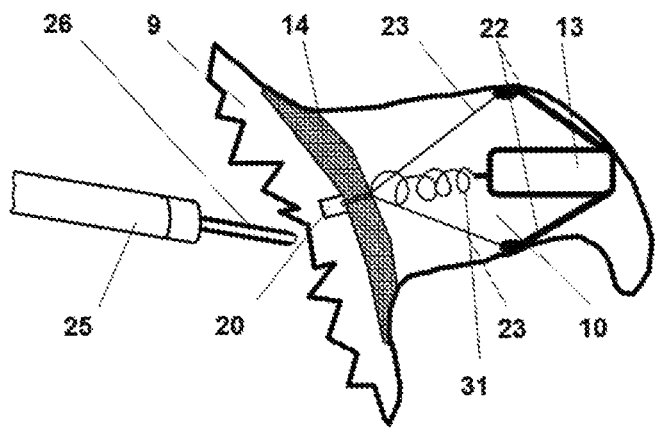
Figure 8:
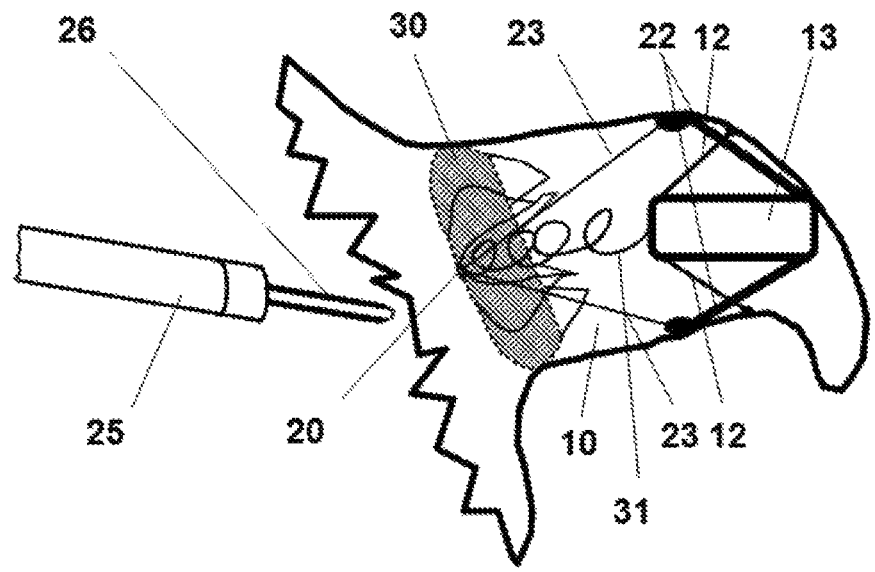
Figure 9:
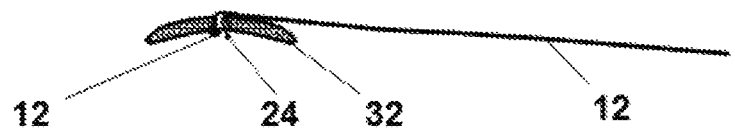
Figure 10:
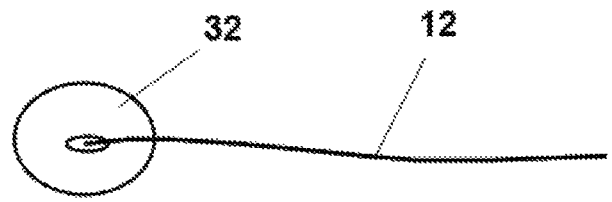
Figure 11:
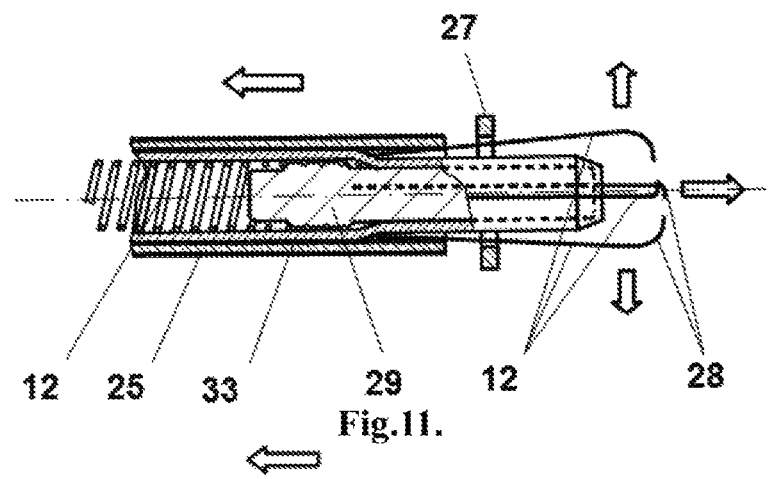
Figure 12:
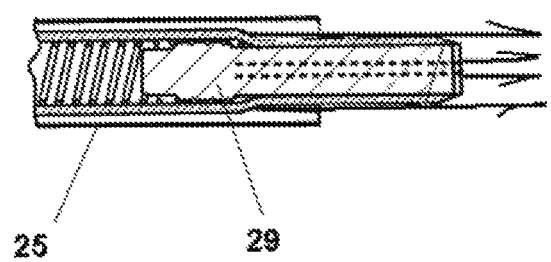
Figure 13:
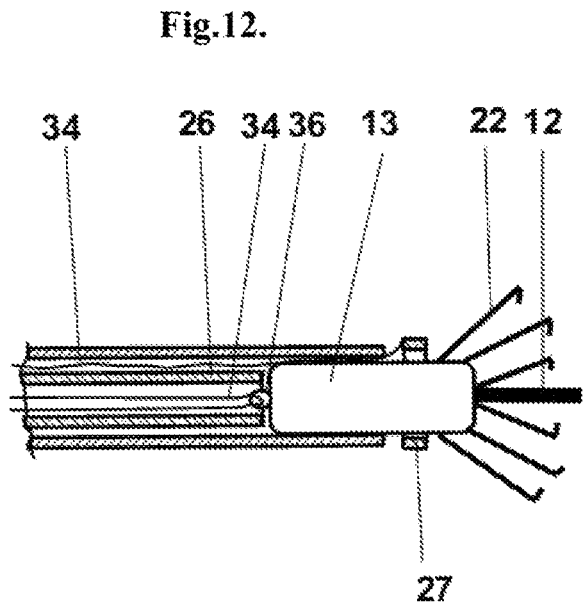
Figure 14:
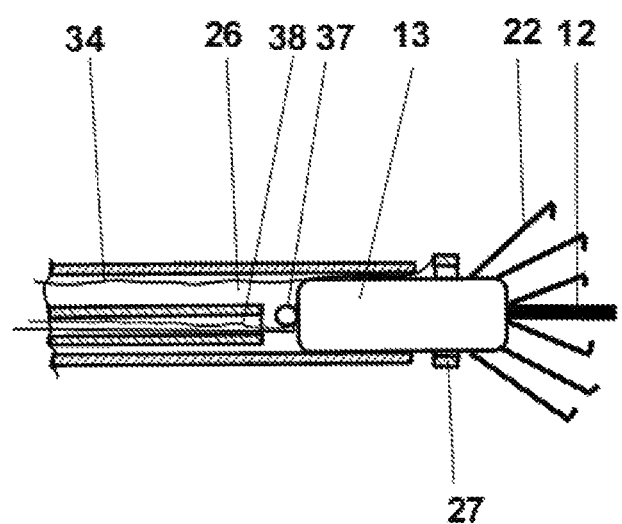
Figure 15:
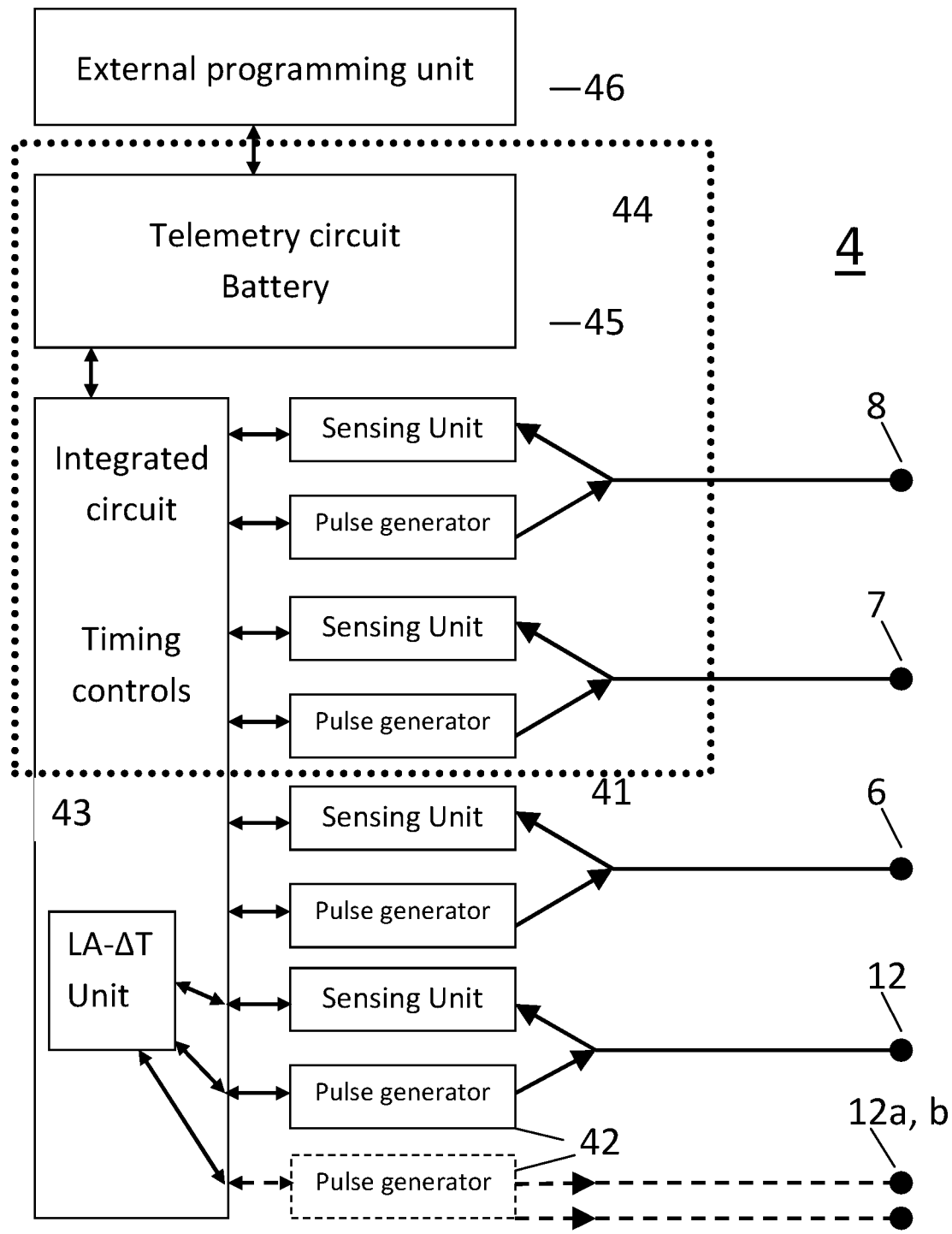
Figure 16:
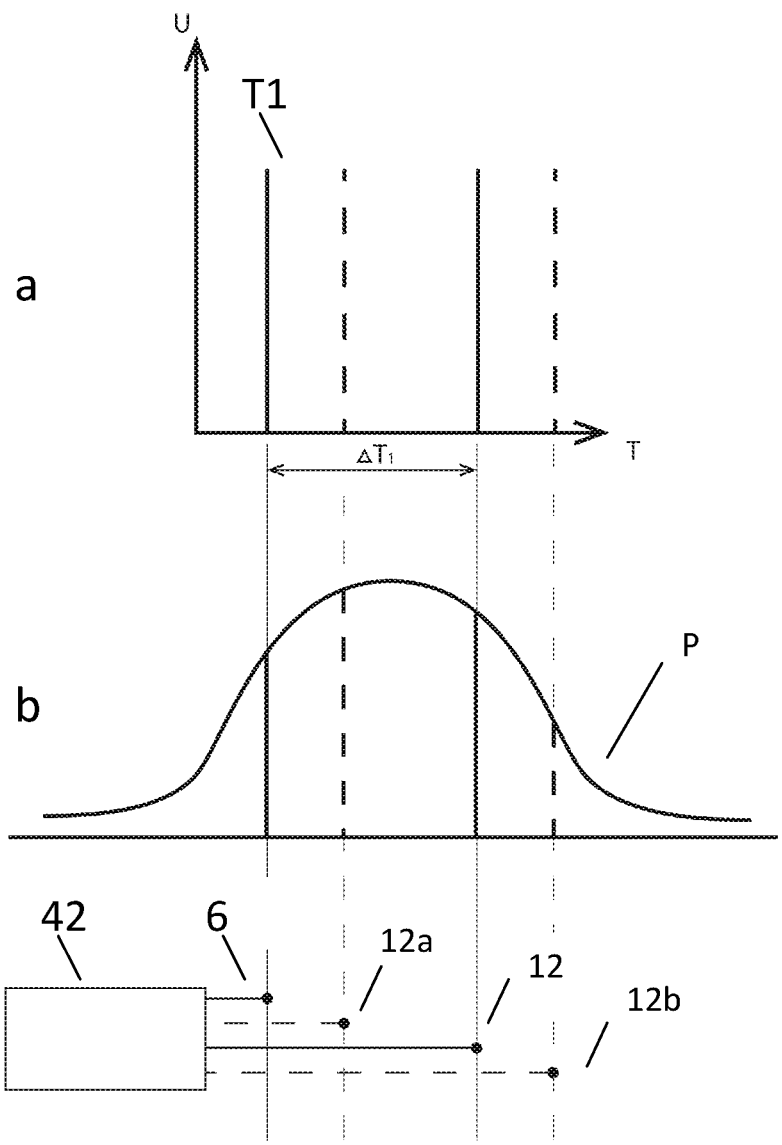

FIG. 6 shows the positioning of the stimulating device 13 having a closing plate 14 and a closing plug 21;

FIG. 7 shows an alternative embodiment of FIG. 6 wherein the closing plug 21 has not been used;

FIG. 8 is a further variation of FIG. 6, wherein the appendage has been closed by a Watchman closing device 30;

FIG. 9 shows the lateral sectional view of a sucking disc electrode 32 (referred also to as a vacuum bell) that can be positioned on a free wall of the heart;

FIG. 10 is the top view of FIG. 9;

FIG. 11 is the sectional view of an electrode clip that can be fixed from the outside having spiral electrode end with a clench tip;

FIG. 12 is a sectional view similar to FIG. 11 in which the electrode elements have respective harpoon tips;

FIG. 13 shows a further embodiment of the designs shown in FIGS. 4 and 5;

FIG. 14 shows a further alternative embodiment of FIG. 13;

FIG. 15 is the simplified block diagram of the apparatus 4 according to the invention;

FIGS. 16a and b show the activation time diagrams corresponding to the positioning of the electrodes indicating also the P wave; and FIGS. 17a and b are time diagrams similar to FIG. 16 showing the stimulation of the left atrial electrodes 12 indicating also the P wave.

Figure 1:
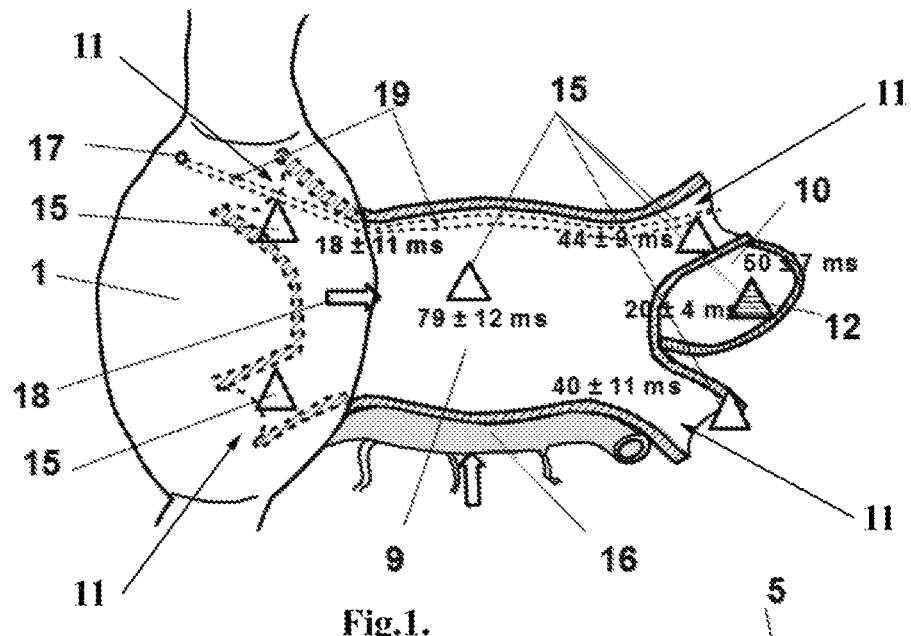
FIG. 1 shows the enlarged sketch of the atrial part of the heart including the visualization of normal propagation times of the stimuli starting from the sinus node.
Figure 2:
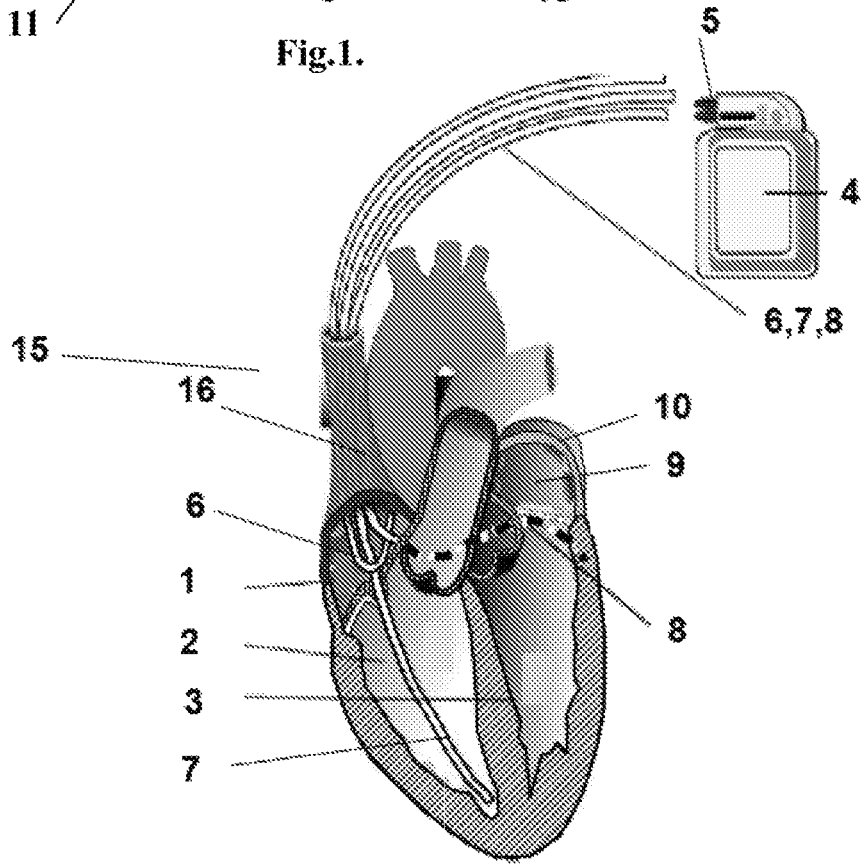
FIG. 2 shows the sectional sketch view of the heart including pacemaker lead electrodes.
Figure 3:
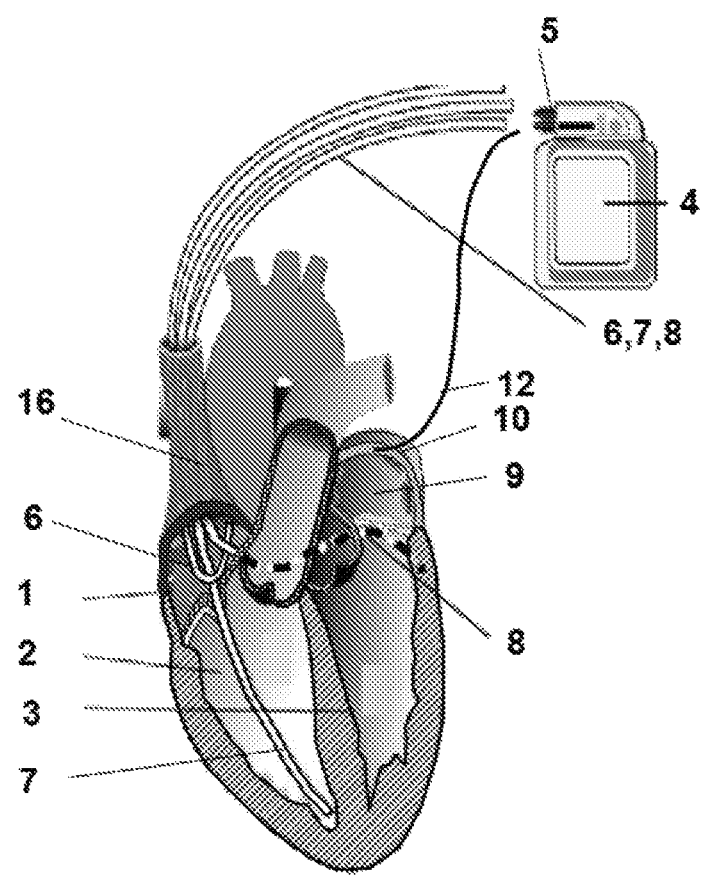
FIG. 3 shows the sketch of the direct stimulation of the left atrium from the outside.

For understanding the method according to the invention the most important parts of the anatomy of the heart and the respective details that have role in leading the stimulus have been illustrated in FIGS. 1-3. FIG. 1 shows primarily the upper part of the heart and there is right atrium 1 and the atrial septum 18 forming the boundary thereof, left atrium 9 positioned beside the right atrium 1, coronary sinus 16 under it and appendage 10 that communicates with the left atrium 9 and lying farthest from the right atrium 1. A separate dashed line indicates Bachmann's bundle 19 that starts from the sinus node 17 in the right atrium 1 and extending towards the remote part of the left atrium 9, furthermore four pulmonary veins 11 were indicated of which three can be seen in the drawing and the fourth one is covered in the rear part.

FIG. 2 shows the sectional view of the heart where one can observe the right atrium 1, right ventricle 2 under it, left ventricle 3 beside it, and above the left ventricle 3 there is the left atrium 9 and the position of the left appendage communicating with the left atrium 9

The stimuli that control the operation of the heart are generated primarily in the sinus node 17.

FIG. 1 shows the normal stimulus propagation times measured from the sinus node 17 of the heart in respective characteristic points. The time data relate to the positions indicated by small triangles in FIG. 1, which designate possible stimulation sites 15 as will be described at later parts of the specification. In FIG. 1 one can observe that certain parts of the left atrium 9 will be stimulated even in case of normal sinus rhythm with a delay of about 100 ms. In FIG. 1 arrows with empty inner parts indicate the sites which have previously been stimulated but from these sites the left atrium 9 can be stimulated only from remote places in an indirect way. These sites i.e. the right side of the atrial septum 18 indicated by the arrow and the portion of the coronary sinus 16 also indicated by an arrow, when being stimulated cannot render the optimized stimulation of the left atrium 9 because of the great distance and the associated propagation delay.

A condition of the basic concept of the present invention lies in that the artificially generated stimulation should be applied in the appropriate site or sites. Such an optimum site is the stimulation of the left atrial appendage 10, and this site was indicated in FIG. 1 by a triangle including horizontal lines. Depending on given anatomical or individual conditions (which will be described later) there can be further preferred stimulation sites 15, and in FIG. 1 the empty triangles in the left atrium 9 indicate such sites. The stimulation site 16 in the appendage 10 defines at the same time the position of electrode 12 which is used for stimulation according to the present invention.

In FIG. 2 in addition to the illustration of the sectional view of the heart a stimulating apparatus 4 has also been shown which will be described in detail in connection with FIG. 15. FIG. 2 shows also the three typical electrodes used for pacemaker function, namely electrode 6 in the right atrium, electrode 7 in the right ventricle and electrode 8 of the left ventricle.

As a starting basis of the solution according to the invention the main grounds of the occurrence of atrial fibrillation will be analyzed. Atrial fibrillation takes place because the propagation speed of the atrial stimulus, because of owing to the subsequent refractory period (a temporary state when stimulation cannot occur) and because the disproportional size of the atrium the natural stimulus cannot stimulate the whole atrial musculature till the end of the refractory period. As a consequence, the inevitably present lower level stimulation loci can "get awaken" and they can trigger the atrial fibrillation. This phenomenon will thus almost automatically take place in case of such an atrial expansion owing to which the stimulus cannot pass through the atrial wall till the end of the refractory period. This phenomenon might take place even with smaller size of the atrium if the fast stimulus-conducting Bachmann's bundle 19 (see FIG. 1) does not function in a satisfactory way, and owing to this fact the area of the atrial musculature that can be stimulated during a depolarization/repolarisation cycle will be smaller. The principle of the drug treatment of atrial fibrillation can be explained easily by the fact that drugs that slow down the propagation of the stimulus and extend the duration of the refractory period, whereby for an uncertain period it can lead to a smaller degree of imbalance occurring in the stimulus propagation/refractory period/physical size.

Such a theory is in accordance with the experience that the ablation of targeted atrial rhythm generating sources can be successful for a transitional period only, since it is only the question of time that from the scars or other sites new stimuli will be generated that trigger the arrhythmia again. With an appropriate drug treatment the return of this process can be delayed.

The fact that previous experiments of stimulating the left atrium could not provide a decisive result can be explained by the fact that a stimulation acting neither at the septum between the two atriums nor from the coronary sinus 16 cannot stimulate all atrial muscles within a single depolarization/repolarisation cycle, thus they cannot prevent the triggering of spontaneous stimuli.

A preferred way of preventing or anticipating atrial fibrillation can be if on makes sure that the whole atrial musculature be stimulated till the end of the refractory period. In case of a sinus rhythm the parts of the left atrium 9 which get activated at the latest time are the left appendage 10, the end regions of the left pulmonary veins and the lower part of the posterior wall of the left atrium 9, and the task is just the appropriate electrical stimulation of these farthest positions of the left atrium 9.

FIG. 3 shows the basis of the apparatus of the present invention, wherein the drawing corresponds substantially to FIG. 2 but in this case the apparatus 4 has a further (or several more) output which is connected to the electrode 12 or to the electrodes placed at appropriate positions of the left atrium 9 and the apparatus makes sure that the electrodes 12 be stimulated in appropriate time slots and with suitable intensity.

Reference is made now to FIG. 15 which shows the simplified block diagram of the apparatus 4 according to the invention. The right atrial electrode 6 is coupled through a wire to input of a sensing unit 41 which detects when a stimulus appears on the right atrial electrode 6 in the form of an electrical voltage and generates a corresponding pulse at its output. The output of the sensing unit 41 is coupled through a delay unit 43 to an input of a pulse generator 42 which at the moment of the output pulse of the delay unit 42 generates a pulse at its own output which has an appropriate voltage and intensity. This output pulse is lead to the electrode 12 which is arranged at the farthest position of the left atrium 9 from the right atrium 1 to stimulate there the left atrium 9. This coupling can be realized either by a wired or a leadless connection. The delay unit 43 is designed to have a sufficient intelligence to adjust the appropriate delay between its input and output pulses as it will be explained later. The delay should be adjustable, and in given cases the adjustment can be realized in a semi-automatic way on the basis of measured ECG parameters, or it can operate in a fully automatic mode but a manual adjustment can also represent a possible way. In case a plurality of electrodes 12 should be coupled to the left atrium 9 which lie in differing distances from the right atrial electrode 6, then it might be required that respective pulses with different delays should be lead to these electrodes 12. Such a possibility has been illustrated in FIG. 15 by the outputs of the pulse generator 42 drawn by dashed lines which outputs are coupled to the electrodes 12a, 12b respectively and the occurrence of the associated pulses might be different from the timing of the pulse lead to the electrode 12. Because the apparatus might have electrodes coupled to different points, and the electrodes can equally have the function of sensing or generating signals, the sensing unit 41 and the pulse generator 42 shown in FIG. 15 have been split into a plurality of sub units that correspond to the number of the electrodes used and these units have been drawn as respective blocks.

It is preferred if the apparatus 4 is complemented also with a pacemaker unit 44 that has a conventional design and it has an input connected to the output of the sensing unit 41, and has respective outputs coupled to the right and left ventricular electrodes 6, 7 and with the electrode 6 itself. The pacemaker unit 44 assumes the stimulation of the heart in case the generation of spontaneous heart triggering pulses are missing or have a delay longer than a predetermined value. The pacemaker unit 44 can also have a defibrillating function.

In FIG. 15 a separate telemetry unit 45 has been shown and a power source is arranged therein and a programming unit 46 that can be built integrally with the apparatus 4 or more frequently as a separate unit coupled through a leadless connection that allows adjustment of different functions and parameters from outside of the patient.

Examples for the operation of the method will be given in connection with FIGS. 16 and 17.

In the diagrams of FIGS. 16a and 16b the first pulse is generated in the moment T1 and this is the natural pulse which is generated spontaneously in the right atrium 1 and it is sensed by the right atrial electrode 6. This pulse stimulates the heart and this is the basic signal of the control according to the present invention. In case such a pulse is not generated spontaneously then it will be artificially generated by the pacemaker unit 44.

According to the invention the remote electrode 12 in the left atrium 9 will be electrically stimulated with a delay, which has a delay $\Delta T1$ relative to the right atrial electrode 6. This is visible in the curve by the fact that the P wave that indicates the atrial electrical activation can be sensed later.

The vertical dashed lines show if in the left atrium 9 in addition to the electrode 12 respective further electrodes 12a and/or 12b are arranged, then owing to their different distances from the right atrium 1 their own activation times can be different, and the stimulation pulses should be lead thereto in differing moments for attaining a uniform reaction of the heart i.e. that occurs at the same time. The diagram b shows how the activation moments of the non-stimulated electrodes are related to the waveform of the measured P wave. Under the diagram the pulse generator 42 has been shown with the electrodes 6 and 12 which are always used and with the optionally applied electrodes 12a and 12b. This example does not exclude the possibility that under given conditions these three electrodes 12a, 12b and 12 be stimulated at the same time.

Figure 17:
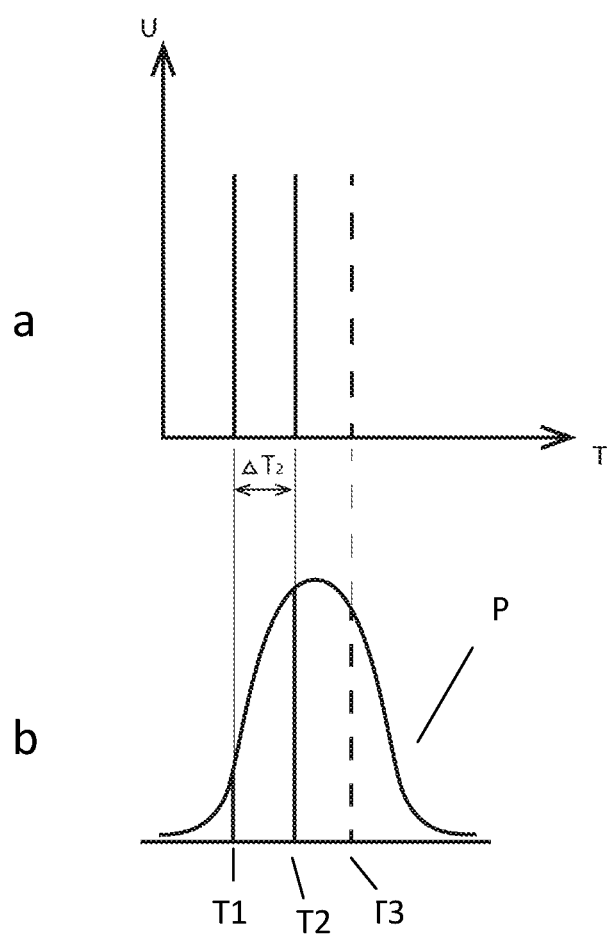

FIG. 17 is similar to FIG. 16 but in this case the left atrial electrode 12 is stimulated with a shorter delay $\Delta T2$ compared to the right atrial electrode 6, and as a result the whole atrial activation time will be shorter and the P wave will be much narrower. The dashed line with the associated moment T3 shows the delay of a further electrode if such is required.

According to the experience collected so far the duration of the delay is within a limit of 150 ms and in extreme situations it can be zero or close to zero. The required delay time can be determined on experimental basis and based on the measured speed of signal propagation in the heart of the patient, and also based on the size of the left atrium 9, but the basis of the control is to obtain the delay that results the shortest atrial activation time, i.e. where the measured ECG signal on the body surface the P wave takes its narrowest value.

During the stimulation according to the invention for preventing atrial arrhythmia it might also happen that based on an algorithm the output leading to the left atrium can be stimulated before the detection or artificial generation of the pulse at the right atrium. This means that the timing might take a negative value therefore the term "delay" used in the present specification might take also a negative value. A basic case of such a "negative" timing if there is no spontaneous stimulation and the atriums are controlled e.g. at a frequency of 60/min in such a way that the stimulation of the left atrium should precede that of the right atrium always by 20 ms. It occurs rarely that the stimulation of the left and right atriums coincide in time. In the everyday practice and in the majority of the cases a positive (i.e. real) delay is required.

Because the anatomy of the heart and the parameters of the propagation of the stimulation pulse in the heart are different at different patients, the number and position of the electrodes that should be coupled to the left atrium might also be different. It is the most preferred and in most of the cases it is also sufficient if a single electrode is coupled to the left appendage 10 or its leadless stimulation is resolved. The number of the required electrodes is determined together by several conditions.

In certain cases it might be required to position in addition to the primarily used left atrial electrode 12 further complementary left atrial electrodes 12a and 12b that can be placed on the outer surface of the left atrium 9 or in the coronary sinus 16.

It has been found that in the heart there is certain proportionality between the electric conduction, the refractory property, the size of the atrium and the required number of electrodes (leads) which is expressed by the following formula:

$$|Ne| \approx Tc/Tn \cdot tn/tr \cdot Sa/Sn$$

where:
Ne: the number of implantable left atrial electrodes 12 i.e. leads (which is an absolute integer),
Tc: measured longest conduction time in between the right and left atrium,
Tn: normal conduction time in between the right and left atrium,
tn: normal time duration of the refractory period,
tr: measured time duration of the refractory period,
   Sa: measured largest diameter of atria,
   Sn: largest diameter of atria measured at a heart that functions regularly Based on the formula it is obtained that the number of electrodes 12 required for stimulating the left atrium is proportional to the size increase of the atria, the extension of the conduction time and the decrease in the length of the refractory period. The absolute value of the product of the mentioned parameters (expressed in integers) defines the number of the electrodes 12 required for the stimulation of the left atrium.

According to the invention the own stimulus of the right atrium 1 is sensed which should be sent in a possible early but appropriate moment as a control stimulating pulse to the electrically far areas of the left atrium 9 including the appendage 10, whereby the speed of propagation of the stimulus will de facto increase and so will the muscular area that can be accessed by the stimulation.

In case the patient needs a pacemaker or it is rather likely that the spontaneous generation of the stimuli might not take place, then it is worthwhile to provide a usual pacemaker function in the apparatus 4, and in that case the stimulation of the electrode 12 is not triggered by the stimulus generated by the sinus node 17 but the right atrial pacemaker beat.

The atrial stimulation realized in this way is referred to as atrial resynchronization. Accordingly the resynchronizing pulse will be forwarded to one or more sites of the left atrium 9 and primarily to the left appendage 10 i.e. to sites which enable that this extra stimulation acts on those parts of the left atrium which by using a natural electrical propagation would reach to those sites slower and with a delay. As a result of the atrial resynchronization the lower level stimulating nodes of the atrial muscles will not be activated, therefore the atrial fibrillation can be treated or anticipated. It should be noted if in a plurality of sites of the left atrium 9 a plurality of electrodes 12 are used, then their stimulation will not necessarily coincide in time, but with an appropriate slight delay depending on the relative positions of the electrodes 12.

The apparatus 4 is capable of stimulating a single or a plurality of sites at any part of the left atrium 9, e.g. by an endocardial and/or myocardial and/or epicardial stimulation of the left appendage 10 and the pulmonary vein 11 and/or the free wall of the left atrium 9 and/or the atrial septum 18 and/or the posterior wall of the left atrium 9 and/or the coronary sinus 16 and/or the epicardial surface of the left atrium 9 and the epicardial surface of the appendage 10 in the left atrium 9.

Because the method according to the invention requires the special placement of the electrodes 12, this necessitates devices and ways of introducing these means which enable this placement in an easy way that requires only a minimum extent of invasive intervention.

In the following part of the specification examples will be given to such devices and the ways of their use.

FIGS. 4 to 8 show how a leadless stimulating device 13 can be introduced and placed into the interior space of the appendage 10 and to provide thereby stimulating pulses to the inner wall of the appendage 10. Earlier it has been mentioned that small size implantable leadless stimulating devices exist by which pacemaker functions can be realized without having wired connection between such a device and the unit that controls it. Because the inner space of the appendage 10 has no role in the function of the heart, whereas according to the invention the most preferred stimulation site is the inner wall of the appendage 10, it seems to be a good solution to place a leadless stimulating device 13 there that can be controlled by the apparatus 4. The energy required for the functioning of the heart rate control device 13 can be provided from the energy of the surrounding parts i.e. using energy harvesting including the utilization of the available kinetic energy, changes in the temperature or of the electromagnetic field, without using a targeted direct energy supply.

For the utilization in the present invention the conventional leadless stimulation devices should be modified in such a way that their shape and size should enable their positioning in the appendage 10 and that they should generate bipolar pulses of sufficient intensity at moments determined by the apparatus 4.

FIG. 4 illustrates the interior of the appendage 10 into which the leadless stimulating device 13 has to be introduced in such a way that in case of need later it can be withdrawn or removed from it. FIG. 4 illustrates an intermediate state of the introduction of the stimulating device 13. The stimulating device 13 is fitted in the forward end section of a flexible introduction sleeve 25 so that its cylindrical body can be arranged completely in the interior of the sleeve 25. In the introduction sleeve 25 behind the stimulating device 13 a pushing part 26 is arranged made also from a flexible tube.

A plurality of discrete positioning and fixing legs 22 are attached around the exterior of the stimulating device 13 which tend to open up in radial direction and have respective end portions that are bent inwardly in an angle or as a curved arc section. In initial state the legs 22 are kept together by a ring 27 arranged behind the forward end of the introduction sleeve 25 therefore their outer diameter in compressed state is not higher than the outer diameter of the introduction sleeve 25. FIG. 4 shows the ring 27 in a distorted scale because it has an outer diameter which is at most as high as the outer diameter of the sleeve 25 thus its presence does not block the introduction. The end of a security wire or filament 34 lead in the interior of the introduction sleeve 25 is fixed to the ring 27. In the extension of the axis of the stimulating device 13 a rod like electrode 12 extends out in forward direction from the body of the device 13 which is insulated from this body. At the rear end of the stimulating device 13 a first part of a pair of fixing hooks 35 is attached, and the other part of the hooks 35 is fixed to the forward end of the pushing part 26, and it is coupled to a long wire that extends in the interior of the pushing part 26 so that it can be pulled from outside past the other end of the part 26.

The size of the pushing part 26 has been designed in such a way that during the introduction of the assembly the engaging parts of the hooks 35 cannot get disengaged as long as the pushing device 26 is not pulled in reverse direction.

In the example shown in FIG. 4 the introduction of the stimulating device 13 into the interior of the appendage 10 takes place as follows: first after the transfixion of the chosen femoral or neck vein the appropriate introduction sleeve 25 is inserted. Then the separation wall between the two atriums 1 and 9 is penetrated by an appropriate needle then the introduction sleeve 25 is inserted into the left atrial appendage 10 in line with standard medical practices. By means of the pushing part 26 in the interior of the sleeve 25 the stimulating device 13 is pushed out in forward direction from the end of the introduction sleeve 25 but during this step the ring 27 is prevented from moving forward, therefore the circularly arranged positioning and fixing legs 22 will expand in outward direction and stabilize the stimulating device 13 in the interior of the appendage 10. The stimulation device 13 will be pushed forward by the pushing part 26 as long as the electrode 12 is pushed against the inner wall of the appendage 12 and gets into a stable contact therewith. The shape of the expanded legs 22 is such that they not only hold the stimulation device 13 but they provide a slight forward bias which ensures a stable contact between the electrode 12 and the inner wall of the appendage 10.

Then the pushing part 26 is pulled in rearward direction and then the two engaged parts of the hooks 35 get disengaged and their connection gets released. Then the introduction sleeve 25 together with the pushing part 26 therein and with the forwardly located ring 27 is pulled out, and the stimulation device 13 remains in the appendage 10 in a stable way. The stimulation device 13 provides the required bipolar pulses in such a way that one of the poles is provided by the legs 22 and the other one by the electrode 12. FIG. 5 shows in a smaller scale the introduction device 13 positioned and fixed in the appendage 10.

In case even after several years if the stimulation device 13 has to be removed, then the removal takes place in reverse order, and for doing it one has to have the two parts of the hooks 35 get repeatedly engaged. To make the positioning and fixing legs 22 removable an end of respective removing filaments 23 are coupled to the legs 22 and the other ends of the filaments 23 is coupled to a small metal body (e.g. to the ring 27 or to the hook 35) which is independent from the stimulation device 13 and it can be caught with a lasso or noose, thereby they can be pulled in rearward direction. When the ring 27 is caught and pulled, then the removing filaments 23 pull and fold in the positioning and fixing legs 22 then after a further pulling movement the whole unit can be removed.

Further possible ways of introducing and removing the stimulation device 13 that provide basically the same function as described above are explained in connection with FIGS. 13 and 14.

In case a small fixing ring 36 is attached to the rear end of the stimulation device 13 as shown in FIG. 13 then for the pulling out it is sufficient to use a double security wire 34 that ensures pulling out so that the security wire 34 should be pulled out by a tubular pushing part 26 that can be attached to the fixing ring 36. When the security wire 34 has been pulled out then the pushing part 26 can also be freely removed.

FIG. 14 shows a different way of introducing and fixing the leadless stimulation device 13. In this embodiment a small fixing ball 37 is attached to the rear end of the stimulation device 13, and on the neck of the ball 37 a small loop or lasso 38 is attached. The wire of the loop 38 is lead out from the body through the interior of a tube designed as the pushing part 26 used to support in a firm way the loop 38 on the fixing ball 37 or a fixing hook 35. When the tube is left loose, the loop 38 will slide out from the fixing ball 37 or from the fixing hook 35 and sets the implanted stimulation device 13 free. The further elements of the assembly are similar to those shown in FIG. 13.

In FIGS. 6 and 7 embodiments similar to those shown in FIGS. 4 and 5 are illustrated but in these cases the inner space of the left atrial appendage 10 is closed by a closing plate 14. In given cases the closure uses also a closing plug 21.

In case of patients where the closure of the appendage is needed the closing plate 14 should be used, where in certain cases the closing plug 21 is also required, and these are designed and placed similar to Amplatzer devices known for men skilled in the art.

The introduction of the stimulation device 13 takes place in a similar way as described in the previous embodiments, but in this case the positioning and fixing legs 22 are designed at the same time as electrodes, therefore the separate axial electrode 12 can be omitted as its role is taken over by certain ones of the positioning and fixing legs 22, which can be arranged to be separately connected to the different poles of the pulses generated by the stimulation device 13.

The appendage closing plate 14 and the self expanding closing plug 21 are preferably connected in a flexible way one after the other. During insertion the positioning and fixing legs 22 are folded back on the leadless heart rhythm controlling stimulation device 13. The self expanding closing plug 21 and the closing plate 14 are made from a flexible metal fabric thus during introduction they are not larger than the stimulation device 13 and in this way all parts can be placed in the interior of the introduction sleeve 25. When the introduction sleeve 25 is introduced into the left atrial appendage 10 i.e. to the intended position, the pushing part 26 is used to push the parts of the assembly, then when the introduction sleeve 25 is pulled back in rearward direction, first the positioning and fixing legs 22, then the closing plug 21 and finally the closing plate 14 will expand. Then following the required control tests the introduction sleeve 25 can be removed together with the pushing part 26.

For the compensation on respective individual shapes of the appendage 10 at different patients it is important that the respective parts be coupled to each other in a flexible way and this is why it is required that the positioning and fixing legs 22 (which take here also the role of the left atrial electrode 12) be connected in a flexible way to the stimulation device 13.

There can be later need for the re-positioning or removal of the stimulation device 13. For having the assembly removable the positioning and fixing legs 22 should be made collapsible or be squeezed. This function is facilitated by the removing filaments 23 which are connected to a fixing element 20. When the fixing element 20 is pulled, then the removing filaments 23 shrink (squeeze) the positioning and fixing legs 22 while the stimulation device 13 remains in its position. The stimulation device 13 will get moved only after the legs 22 have been squeezed when the device 13 has been pulled by a connection filament 31.

FIG. 7 differs from the embodiment of FIG. 6 in the lack of using a separate closing plug 21 and the appendage 10 is closed only by the closing plate 14. Because the closing plate 14 is also made from a flexible metal fabric therefore its placement takes place in the same way.

In FIG. 8 a further way of placing and fixing a heart rate control leadless stimulation device 13 in the left atrial appendage 10 is shown, in which instead of the closing plate 14 a per se known Watchman closing device 30 has been used. In this embodiment there are circularly arranged, flexibly expanding positioning and fixing legs 22 that extend in rearward direction which are oppositely positioned with respect to a plurality of the atrial electrodes 12.

In order for a potentially required re-positioning, the device can be pulled back into the introduction sleeve 25 again and the removing filaments 23 are used which are connected to the positioning and fixing legs 22. By pulling the filaments 23 the legs 22 will be pulled to the body of the stimulation device 13, whereby the legs and the body can be retracted into the sleeve 25. In this case owing to the reverse orientation the electrodes 12 will automatically get squeezed to the body.

When the implant is positioned to the intended site and it was checked and tested that it has been appropriately fixed, it will be finally separated from the pushing part 26. Then the introduction sleeve 25 is removed together with the pushing part 26, and the operation is completed by the treatment of the site of entry.

The previously described ways of using the leadless stimulation device 13 in the appendage 10 is not the only way of connecting the stimulating electrical signal to the left atrium 9 but it can be provided by means of a left atrial electrode 12 lead there from exterior direction. The design and fixing of the exterior positioning and fixing of the left atrial electrode 12 a number of embodiments will now be shown and described with reference to FIGS. 9 to 12.

FIG. 9 shows the design and fixation of an electrode in sectional view that has a suction disc 32 that can be rolled or wound together and the top view of the disc 32 in unwound state is shown in FIG. 10. The external surfaces of the atria and the ventricles which can be approached from the pericardium can be accessed by minimal invasive surgery or by a percutan stitching made under the pericardium or close to the apex cordis. The electrode sits and it is supported on the exterior heart surface by means of the unfolded suction disc 32 which is wound in longitudinal direction during introduction. The wound suction disc 32 (made e.g. by silicone rubber) can be introduced through a small cross section, then at the pericardium it is unwound and turned towards the heart with its suction side. A suction tube with small diameter is coupled to the centre of the suction disc 32 through which a sufficient negative pressure (suction) can be established after it has taken the required position. For the sake of better illustration FIGS. 9 and 10 do not show the way how the suction disc 32 is introduced. The essence here lies in that the suction disc 32 together with the electrode 12 arranged therein can be pushed and oriented to the appropriate site. In this case the electrode 12 is designed as having a tined tip forming an electrode hook 24. After the suction disc 32 has been positioned to the required outer site of the pericardium then the open suction disc 32 gets adhered to the given large area and then through the central tube a suction is provided resulting in that the suction disc 32 will get pressed to the selected area enabling that the centrally arranged tined electrode hook 24 be pressed into the heart muscles. Following the termination of the sucking effect the suction disc 32 is held by the hook 24 which has then a stable engagement with the heart muscles. The height of the suction disc 32 is chosen in such a way to protect the electrode hook 24 and till the start of the suction it should not hurt the heart.

In the top view of FIG. 10 it can be seen that the suction disc 32 has an oval shaped central opening for providing more space to the electrode hook 24. In the hooked or tined coupling the final position fixing is provided by the electrode hook 24 (i.e. not only the vacuum which exists only for a transitional period).

The suction disc 32 covers the electrode and ensures that the tip of the hook 24 cannot hurt the heart during penetration and introduction, but only when the electrode hook 24 arrives in the required position the effect of the vacuum generates the piercing force. Thereafter the vacuum is not required any further. The electrode hook 24 is electrically connected to the apparatus 4.

FIG. 11 shows an electrode clip 29 that can be fixed from the exterior to the wall of the left atrial appendage 10 or to other sites of the heart that has a plurality of clench tips 28 which are inwardly and partially bent at their tips which project slightly forward, whereby the tips can be stuck in the heart tissues. The left atrial electrode 12 shown in the drawing is in fact a tubular spiral spring assembly covered at the outside by a thin plastic coating 33 (molten silicone). It is very flexible because this is required that owing to the movement of the heart no tiredness breakage can take place. The spirally wound steel does not contact the heart muscle directly but there is an end part fitted in the spiral. The spiral has a hollow interior in order to enable insertion of a stiffening wire if such is needed to facilitates introduction, then when the fixing electrode clip 29 has been positioned, it can be removed (if it had been kept therein, it would be coupled to the heart with a rather stiff way and it could perhaps pierce the heart).

The left atrial electrode 12 can be introduced as arranged in the introduction sleeve 25 shown in the drawing as long as it reaches the heart. Then by pulling the sleeve 25 back or by pushing the electrode slightly further the resilient clenches beyond the end of the electrode get expanded. By pushing the electrode in forward direction the tips of the clenches reach the tissues, and then the introduction sleeve 25 is pushed forward resulting in the squeezing of the clenches that get hooked and kept in the tissues. When the electrode is fixed finally in this position, a remaining ring 27 is pushed forward by means of the introduction sleeve 25 as long as the ring 27 sufficiently closes the electrode clenches 28 which is required for a stable positioning.

FIG. 12 shows an electrode clip 29 that can be fixed from the exterior to the wall of the left atrial appendage 10 or to other sites that has harpoon-like electrodes. This embodiment differs from the one described in connection with FIG. 11 in that instead of the electrode clenches 28 their tips is designed like a harpoon. If the electrodes have sharp but harpoon like tips, then the beard of the harpoon and its oblique shape might fix the tips and there is no need of using a fixing ring 27.

All of the previously mentioned electrodes and stimulated surfaces can be coated by a steroid anti inflammatory substance to prevent scar development and a later increase of the electrical stimulation threshold.

By using the resynchronization according to the invention the atrial fibrillation can be persistently terminated, the symptoms disappear and the need for hospitalization decreases, and substantial side effects and complications (stroke or heart insufficiency) can be anticipated. The use of the present invention decreases the chances of repeated occurrence of atrial fibrillation and facilitates the return of the sinus rhythm even in case of previously existed atrial fibrillation. Together with the left atrial appendage closure devices or built with them together it decreases the occurrence of heart based embolic strokes. By the atrial stimulation at several sites the disorders of the atrial electrical stimulations can be decreased even during atrial fibrillation. By means of the atrial resynchronization pacemaker treatment and electrical reverse remodelling can be attained.

By the overdrive stimulation of the left atrial appendage the shortening of the refractory sections of the pulmonary veins (primarily at the left side) and of the surrounding muscles can be anticipated, the formation of the atrial short-long-short periodicity can be prevented which per se decreases the inclination of the patients to atrial fibrillation. The lower level stimulation generating nodes of the atrial musculature cannot become activated, whereby the atrial fibrillation can be prevented or treated.

The invention claimed is:

1. An apparatus for long term heart rhythm normalization for patients inclined to having atrial fibrillation, configured to be positioned in a body of a patient comprising a first leadless electrode placed in a right atrium the apparatus senses primary electrical pulses generated in the right atrium and comprises a sensing unit coupled to the first electrode and also comprises a pulse generator that generates stimulating pulses in moments related to time of occurrence of sensed primary pulses, the pulse generator is in leadless connection with a second electrode placed in contact with and stimulates a left atrial appendage of the patient, wherein the pulse generator generates stimulating pulses being delayed in time relative to moments of the primary pulses and further comprising a unit that senses intracardial activation time by a P wave of a heart of the patient, said P wave having a width, for controlling said delay in time of said generated pulses lead to said second electrode and adjusts thereby the width of the P wave to a minimum or close to the minimum.

2. The apparatus as claimed in claim 1, wherein the heart further comprises at least one wall, having an interior and exterior, and in addition to said second electrode at least one additional electrode is coupled to one or more different portions of the exterior of the heart wall at or close to the left atrial appendage, and said pulse generator has at least one further output connected to said at least one additional electrode, by which different portions of the left atrial appendage of the patient are stimulated, and respective slightly differing delay times are associated with the stimulating pulses of the respective outputs.

3. The apparatus as claimed in claim 1, wherein said second electrode is part of a leadless stimulating device having a sufficiently small size to be inserted through an opening and placed in the interior of the left atrial appendage of the patient and leads stimulating pulses to an inner wall of the left atrial appendage.

4. The apparatus as claimed in claim 3, wherein the stimulating device comprises legs that stabilize, position and fix the arrangement of the device in the left atrial appendage and the legs are abutting the inner wall of the left atrial appendage and the legs tend to expand in a flexible way and can be squeezed by a ring.

5. The apparatus as claimed in claim 3, wherein the leadless stimulating device comprises an electrode or a plurality of electrodes which are biased in a flexible way to the inner wall of the left atrial appendage and which open up or extend in a resilient way in a direction opposite to fixing legs.

6. The apparatus as claimed in claim 3, wherein a hook or fixing screw element or a connection filament is coupled to the rear end part of the stimulating device arranged in the left atrial appendage.

7. The apparatus as claimed in claim 2, wherein the at least one additional electrode is designed as an electrode clip fixing a position of the electrode and being biased by a spiral spring, and the electrode clip comprises a plurality of circularly arranged clench tips having forward edges bent towards the heart wall, and the clench tips tend to get flexibly expanded and being surrounded by a ring, and the retraction of the clench tips with respect to the ring pushes the edges of the clench tips in the heart muscles and provides a durable contact therewith.

8. The apparatus as claimed in claim 2, wherein the at least one additional electrode is biased by a spiral spring and comprises electrode tines or harpoons at their tips that can be pushed in forward direction to get penetrated into the heart wall and to established a durable contact therewith.

9. An apparatus for long term heart rhythm normalization for patients inclined to having atrial fibrillation, configured to be positioned in a body of a patient comprising a first wired electrode placed in a right atrium the apparatus senses primary electrical pulses generated in the right atrium and comprises a sensing unit coupled to the first electrode and also comprises a pulse generator that generates stimulating pulses in moments related to time of occurrence of sensed primary pulses, the pulse generator is in wired connection with a second electrode placed in contact with and stimulates a left atrial appendage of the patient, wherein the pulse generator generates stimulating pulses being delayed in time relative to moments of the primary pulses and further comprising a unit that senses intracardial activation time by a P wave of a heart of the patient, said P wave having a width, for controlling said delay in time of said generated pulses lead to said second electrode and adjusts thereby the width of the P wave to a minimum or close to the minimum.

10. An apparatus for long term heart rhythm normalization for patients inclined to having atrial fibrillation, configured to be positioned in a body of a patient comprising a first leadless electrode placed in a right atrium the apparatus senses primary electrical pulses generated in the right atrium and comprises a sensing unit coupled to the first electrode and also comprises a pulse generator that generates stimulating pulses in moments related to time of occurrence of sensed primary pulses, the pulse generator is in leadless connection with a second electrode placed in contact with and stimulates a left atrial appendage of the patient, and a closing device for closing an opening of the left atrial appendage behind said leadless stimulating device, wherein the pulse generator generates stimulating pulses being delayed in time relative to moments of the primary pulses and further comprising a unit that senses intracardial activation time by a P wave of a heart of the patient, said P wave having a width, for controlling said delay in time of said generated pulses lead to said second electrode and adjusts thereby the width of the P wave to a minimum or close to the minimum, and wherein said second electrode is part of a leadless stimulating device having a sufficiently small size to be inserted through an opening and placed in the interior of the left atrial appendage of the patient and leads stimulating pulses to an inner wall of the left atrial appendage.

11. An apparatus for long term heart rhythm normalization for patients inclined to having atrial fibrillation, configured to be positioned in a body of a patient comprising a first leadless electrode placed in a right atrium the apparatus senses primary electrical pulses generated in the right atrium and comprises a sensing unit coupled to the first electrode and also comprises a pulse generator that generates stimulating pulses in moments related to time of occurrence of sensed primary pulses, the pulse generator is in leadless connection with a second electrode placed in contact with and stimulates a left atrial appendage of the patient, wherein the pulse generator generates stimulating pulses being delayed in time relative to moments of the primary pulses and further comprising a unit that senses intracardial activation time by a P wave of a heart of the patient, said P wave having a width, for controlling said delay in time of said generated pulses lead to said second electrode and adjusts thereby the width of the P wave to a minimum or close to the minimum, wherein the heart further comprises at least one wall, having an interior and exterior, and in addition to said second electrode at least one additional electrode is coupled to one or more different portions of the exterior of the heart wall at or close to the left atrial appendage, and said pulse generator has at least one further output connected to said at least one additional electrode, by which different portions of the left atrial appendage of the patient are stimulated, and respective slightly differing delay times are associated with the stimulating pulses of the respective outputs, and wherein said at least one additional electrode comprises an initially rolled then opened suction disc, having a central opening, said suction disc can be positioned to a targeted portion of an outer heart wall, a suction tube is coupled to the central opening of the suction disc, the suction tube having an interior and a wire is lead in the interior of the suction tube, and an electrode hook is provided at the tip of the wire, and when the suction disc gets sucked then the electrode hook is pressed into the outer heart wall in a given depth where it stops and gets into electrical contact with the outer heart wall.

12. The apparatus as claimed in claim 11, wherein said central opening has an elongated form.

13. The apparatus as claimed in claim 1, wherein the second electrode is dimensioned to fit stably inside the left atrial appendage of the patient.

14. The apparatus as claimed in claim 9, wherein the second electrode is dimensioned to fit stably inside the left atrial appendage of the patient.

* * * * *